(12) United States Patent
Peterson et al.

(10) Patent No.: US 12,605,269 B1
(45) Date of Patent: Apr. 21, 2026

(54) URINARY CATHETER URINE COLLECTION BAG WITH REPLACEABLE DRAIN BLOCKAGE FILTER

(71) Applicants: Shelby Elizabeth Peterson, Mountain Iron, MN (US); Benjamin Daniel Wilson, Goodyear, AZ (US); Brianna Vance, Gilbert, AZ (US); Christina Hassib Aridi, Gilbert, AZ (US); Natalia Evelyn Duran Valenzuela, Phoenix, AZ (US); Hannah Jane Oman, Chandler, AZ (US)

(72) Inventors: Shelby Elizabeth Peterson, Mountain Iron, MN (US); Benjamin Daniel Wilson, Goodyear, AZ (US); Brianna Vance, Gilbert, AZ (US); Christina Hassib Aridi, Gilbert, AZ (US); Natalia Evelyn Duran Valenzuela, Phoenix, AZ (US); Hannah Jane Oman, Chandler, AZ (US)

( * ) Notice: Subject to any disclaimer, the term of this patent is extended or adjusted under 35 U.S.C. 154(b) by 424 days.

(21) Appl. No.: 18/479,399

(22) Filed: Oct. 2, 2023

Related U.S. Application Data

(60) Provisional application No. 63/379,606, filed on Oct. 14, 2022.

(51) Int. Cl.
*A61M 25/00* (2006.01)
*A61F 5/44* (2006.01)
(52) U.S. Cl.
CPC ....... *A61F 5/4405* (2013.01); *A61M 25/0017* (2013.01)
(58) Field of Classification Search
CPC ........ A61F 5/4405; A61F 5/441; A61F 2/013;

A61F 2/01; A61M 25/0017; A61M 2210/1085; A61M 25/10; A61M 1/84; A61M 2039/248; A61M 2205/75; A61M 60/851; A61M 1/60; A61M 1/63;
(Continued)

(56) References Cited

U.S. PATENT DOCUMENTS

| | | | | |
|---|---|---|---|---|
| 4,801,292 A | * | 1/1989 | Watson | A61M 3/0229 |
| | | | | 604/185 |
| 4,997,435 A | * | 3/1991 | Demeter | A61B 17/22 |
| | | | | 606/127 |

(Continued)

FOREIGN PATENT DOCUMENTS

EP 0202384 A1 * 11/1986 ............ A61M 1/772

*Primary Examiner* — Rebecca E Eisenberg
*Assistant Examiner* — Brandon W. Levy
(74) *Attorney, Agent, or Firm* — Kenneth C. Booth; Booth Udall, PLC

(57) ABSTRACT

A urinary catheter urine collection system with a urinary catheter fluidly coupled to a bag inlet to pass urine from a patient to the bag. A drainage tube fluidly coupled to a bag outlet to pass urine out of the bag. A removable blockage filter between the bag and the drainage tube to filter the urine passing through the drainage tube, the blockage filter having a cup, cup wall and a plurality of wall slits. A flow valve removably positioned between the bag and the blockage filter to selectively block urine flow to the blockage filter, with open and closed configurations. In use, the catheter is inserted into the patient to drain urine from the patient to the bag, and blockage material in the urine is filtered from the urine with the blockage filter as the urine is passed from the bag.

20 Claims, 8 Drawing Sheets

(58) Field of Classification Search
CPC .......... A61M 1/631; A61M 1/64; A61M 1/70;
A61M 1/71; A61M 1/69; A61M
2210/1082; A61M 25/0082; A61M 1/79;
A61B 2217/005; A61B 2017/22079;
A61B 2034/301; A61B 17/22; A61B
2018/00511; A61B 18/24
See application file for complete search history.

(56) References Cited

U.S. PATENT DOCUMENTS

| | | | |
|---|---|---|---|
| 6,471,680 B1 * | 10/2002 | Cawood ................ | A61F 5/4405 |
| | | | 604/327 |
| 2018/0303655 A1 * | 10/2018 | Glithero ................ | A61L 29/146 |

* cited by examiner

URINARY CATHETER URINE COLLECTION BAG WITH REPLACEABLE DRAIN BLOCKAGE FILTER

CROSS REFERENCE TO RELATED APPLICATIONS

This application claims the benefit of the filing date of U.S. Provisional Patent Application 63/379,606 entitled "URINARY CATHETER URINE COLLECTION BAG WITH REPLACEABLE DRAIN BLOCKAGE FILTER" to Peterson, et al. that was filed on Oct. 14, 2022, the disclosure of which is hereby incorporated herein by this reference.

TECHNICAL FIELD

Aspects of this document relate generally to a urinary catheter urine collection bag, and more specifically to urinary catheter urine collection bag with a replaceable drain blockage filter.

BACKGROUND

According to the CDC ("Center for Disease Control"), an estimated 75% of all urinary tract infections ("UTIs") inside a hospital are caused by urinary catheters, also known as Foley catheters. Blockages of urinary catheters caused by blood, bacteria, and mineral deposits can lead to complications with in-care and out-care patient treatment. Each catheter connects to a collection bag for urine drainage. The healthcare professional may empty the collection bag of urine while the collection bag is still attached to the patient through a spout at the base of the bag.

Often however, because many patients needing a urinary catheter are in the hospital due to trauma or surgery, the patient has blood in their urine, including blood clots. Other blockages can also form in the collection bag through bacteria and mineral deposits. The blockages settle at the bottom of the bag before draining. The build-up of blockage material at the bottom of the bag often blocks the drain tube and hinders the healthcare professional from emptying the collection bag. To remove the blockage material buildup, healthcare professionals currently manipulate the blockage materials by handling the bag and pushing clots out of the way to drain the urine, which is not always effective or only temporarily effective until the number or magnitude of the blockage materials exceeds the ability to push them out of the way. When manual manipulation fails to allow for draining around the blockage materials, the healthcare professional is required to remove the urinary catheter from the patient entirely and replace it with a new one. Removal of a blocked urinary catheter and attachment of a new urinary catheter is not only uncomfortable and sometimes painful for the patient, it causes an increased likelihood of UTIs.

There are currently no known, effective methods or devices on the market for removing blood clot blockages in a urinary catheter collection bag drain. The problem is well known and persistent since the introduction of urinary catheters to the extent that methods have been developed, such as by using a dye, to inform healthcare professionals when an infection is imminent, and pre-treating patients with antibiotics in catheter systems to reduce the likelihood of UTIs. However, overuse of antibiotics increases antibiotic resistance and the likelihood of development of superbug infections and are, thus, undesirable.

SUMMARY

Aspects of this document relate to a urinary catheter urine collection bag assembly, comprising a bag having an upper end with an inlet and a lower end opposite the upper end with an outlet, a urinary catheter fluidly coupled to the inlet and configured to pass urine from a patient to the bag, a drainage tube fluidly coupled to the outlet and configured to pass urine out of the bag, a removable blockage filter positioned between the bag and the drainage tube and configured to filter the urine before the urine passes through the drainage tube, the blockage filter having a cup with a cup wall and a plurality of slits extending through the cup wall, and a flow valve positioned between the bag and the blockage filter and removably coupled to the blockage filter, wherein the flow valve is configured to selectively block the flow of urine from the bag to the blockage filter, the flow valve having an open configuration in which the flow of urine through the flow valve is permitted and a closed configuration in which the flow of urine through the flow valve is stopped.

Particular embodiments may comprise one or more of the following features. The flow valve may be a one-way valve. The blockage filter may further have a filter housing fluidly coupled to the drainage tube, wherein the cup is configured to sit inside of the filter housing. The flow valve may have a body and at least one valve arm slidably coupled with a corresponding opening in the body, wherein when the flow valve is moved from the open configuration to the closed configuration, the at least one valve arm is moved further into the corresponding opening. When the flow valve is moved from the closed configuration to the open configuration, the corresponding opening may be configured to remove buildup on the at least one valve arm from the at least one valve arm.

Aspects of this document relate to a urinary catheter urine collection bag assembly, comprising a bag having a lower end with an outlet, a urinary catheter fluidly coupled to the bag and configured to pass urine from a patient to the bag, a drainage tube fluidly coupled to the outlet and configured to pass urine out of the bag, and a blockage filter positioned between the bag and the drainage tube and configured to filter the urine before the urine passes through the drainage tube.

Particular embodiments may comprise one or more of the following features. The blockage filter may be removable. The blockage filter may have a cup with a cup wall and a plurality of slits extending through the cup wall. The blockage filter may further have a filter housing fluidly coupled to the drainage tube, wherein the cup is configured to sit inside of the filter housing. A flow valve positioned between the bag and the blockage filter and removably coupled to the blockage filter, wherein the flow valve is configured to selectively block the flow of urine from the bag to the blockage filter. The flow valve may have an open configuration in which the flow of urine through the flow valve is permitted and a closed configuration in which the flow of urine through the flow valve is stopped. The flow valve may have a body and at least one valve arm slidably coupled with a corresponding opening in the body, wherein when the flow valve is moved from the open configuration to the closed configuration, the at least one valve arm is moved further into the corresponding opening. When the flow valve is moved from the closed configuration to the open configuration, the corresponding opening may be configured to remove buildup on the at least one valve arm from the at least one valve arm. The flow valve may be a one-way valve.

Aspects of this document relate to a method of draining urine from a patient, comprising inserting a catheter into the patient, draining urine from the patient through the catheter, collecting the urine in a urine collection bag, filtering blockage material out of the urine with a blockage filter after collecting the urine in the urine collection bag, and passing the urine out of the collection bag.

Particular embodiments may comprise one or more of the following features. Replacing the blockage filter with a replacement blockage filter. The blockage filter may be positioned between the collection bag and a drainage tube. Moving a valve to a closed configuration to stop flow of urine through the blockage filter. Replacing the blockage filter with a replacement blockage filter after moving the valve to the closed configuration. Moving the valve to an open configuration to allow flow of urine through the replacement blockage filter after replacing the blockage filter with the replacement blockage filter.

The foregoing and other aspects, features, and advantages will be apparent from the specification, drawings, and the claims.

BRIEF DESCRIPTION OF THE DRAWINGS

Implementations will hereinafter be described in conjunction with the appended drawings, where like designations denote like elements, and.

Figure 1:
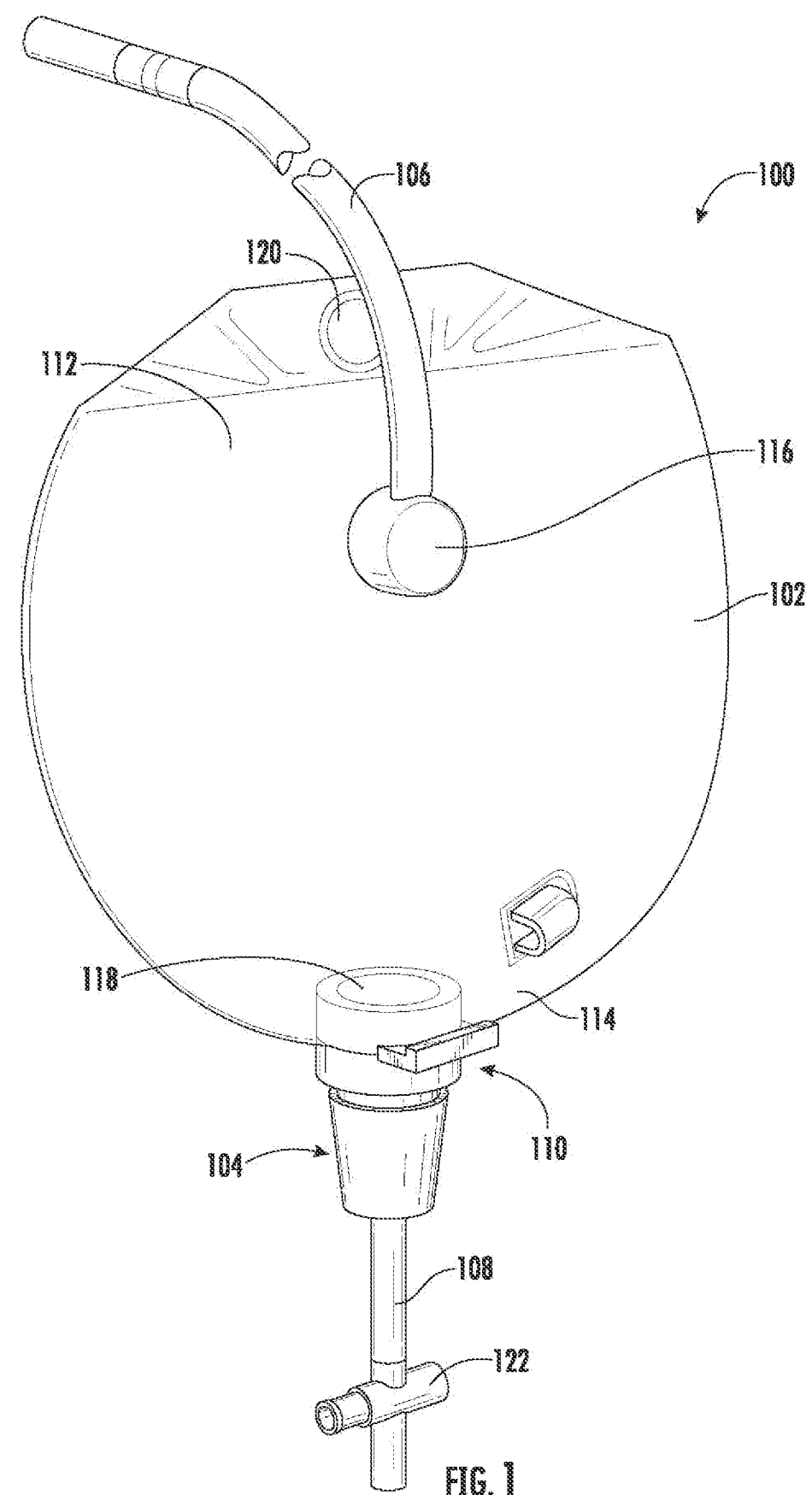
FIG. 1 is a perspective view of a urinary catheter urine collection bag assembly.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of implementations.

DETAILED DESCRIPTION

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

Throughout the description and claims of this specification, the words "comprise" and "contain" and variations of the words, for example "comprising" and "comprises", mean "including but not limited to", and are not intended to (and do not) exclude other components.

As required, detailed embodiments of the present disclosure are included herein. It is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the disclosure to be better understood. However, they are given merely by way of guidance and do not imply any limitation.

The present disclosure may be understood more readily by reference to the following detailed description taken in connection with the accompanying figures and examples, which form a part of this disclosure. It is to be understood that this disclosure is not limited to the specific materials, devices, methods, applications, conditions, or parameters described and/or shown herein, and that the terminology used herein is for the purpose of describing particular embodiments by way of example only and is not intended to be limiting of the claimed inventions. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

More specifically, this disclosure, its aspects and embodiments, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The present disclosure is related to a urinary catheter urine collection bag assembly 100 with a bag 102 and a blockage filter 104 that is configured to capture blood clots, bacteria, minerals, and other blockage material settling to the bottom of the bag 102. Thus, when urine is drained out of the bag 102, the blockage material is limited in its ability to block the drainage tube 108 because the blockage material has been gathered out of the urine by the blockage filter 104 before the urine passes through the drainage tube 108. Thus, the urine collection bag assembly 100 is designed to increase the amount of time that a urinary catheter remains useful and decrease the need for placement of a new catheter and the accompanying increased likelihood of a UTI or other infection.

As shown in FIG. 1, the urine collection bag assembly 100 may comprise a bag 102, a blockage filter 104, a urinary catheter 106, a drainage tube 108, and a flow valve 110. Some embodiments of the urine collection bag assembly 100 may exclude some of these components and other components may be added.

The bag 102 may have an upper end 112 and a lower end 114 opposite the upper end 112. The upper end 112 may have an inlet 116 into the bag 102 and the lower end 114 may have an outlet 118 out of the bag 102. However, in other embodiments, the inlet 116 and the outlet 118 may be positioned in any other position on the bag 102. The bag 102 may have any shape and may have a hook, loop or other type of hanger 120 at the upper end 112 to provide a convenient way to suspend the bag 102 from a supporting structure. Because the blockage material sometimes settles out of the urine over a period of time, the blockage filter 104 may be positioned such that, when the bag 102 is suspended from the hanger 120, the blockage filter 104 is positioned below the hanger 120. However, other embodiments are also contemplated. Although FIG. 1 illustrates the blockage filter 104 facing downward, for convenience, this orientation is not required for functionality of the collection bag assembly 100.

The urinary catheter 106 may be fluidly coupled to the inlet 116 of the bag 102 such that when fluid, such as urine, flows through the urinary catheter 106 to the bag 102, the urine exits the catheter 106 and enters the bag 102 through the inlet 116. Thus, the urinary catheter 106 may be configured to pass urine from a patient to the bag 102. The urinary catheter 106 may be any size, any length, and any shape. In some embodiments, as shown in FIG. 1, an optional urinary catheter 106 catch, shown above reference number 114, may be included for convenience that is sized and configured to receive the urinary catheter 106 and hold it in place against the bag 102 when not in use.

The drainage tube 108 may be fluidly coupled to the outlet 118 and may be configured to pass urine out of the bag 102. The drainage tube 108 may have a stop 122 that restricts the flow of urine through the drainage tube 108, such as a clamp, a crimping mechanism, or a valve. The function of the stop 122 is simply to allow the user of the urine collection bag assembly 100 to decide when to allow urine to drain out of the bag 102. Thus, the catheter 106, the inlet 116 of the bag 102, the bag 102 itself, the outlet 118 of the bag 102, and the drainage tube 108 may all be actively fluidly coupled together without the urine draining out through the drainage tube 108 because the stop 122 restricts the flow.

As described above, the drainage tube 108 sometimes becomes blocked by blood clots and other blockages that form in the urine. Thus, before the urine passes through the drainage tube 108, the blockage filter 104 may be configured to filter the urine to remove any potential blockages. The blockage filter 104 may be positioned between the bag 102 and the drainage tube 108 such that urine must pass through the blockage filter 104 to reach the drainage tube 108 and empty out of the bag 102.

Figure 2:
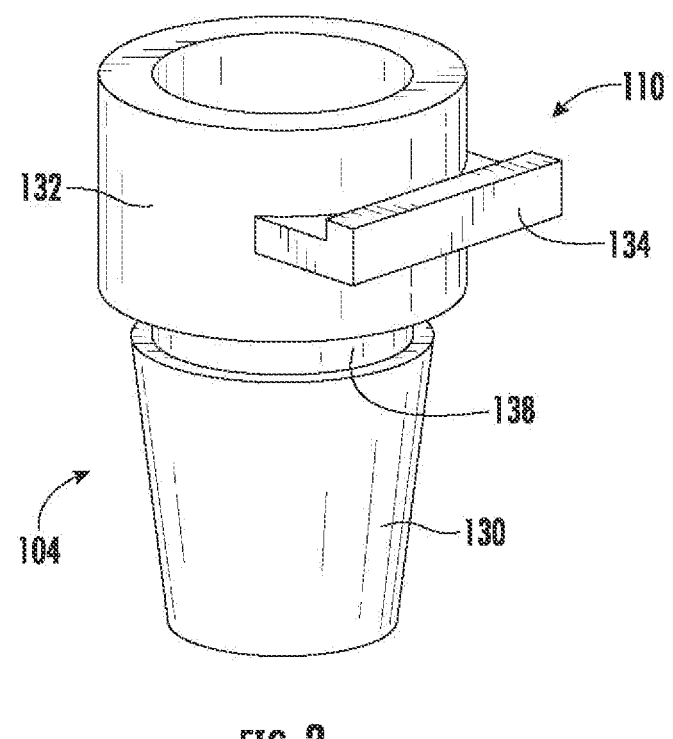
FIG. 2 is a perspective view of a filter assembly of the urine collection bag assembly shown in FIG. 1.
Figure 3:
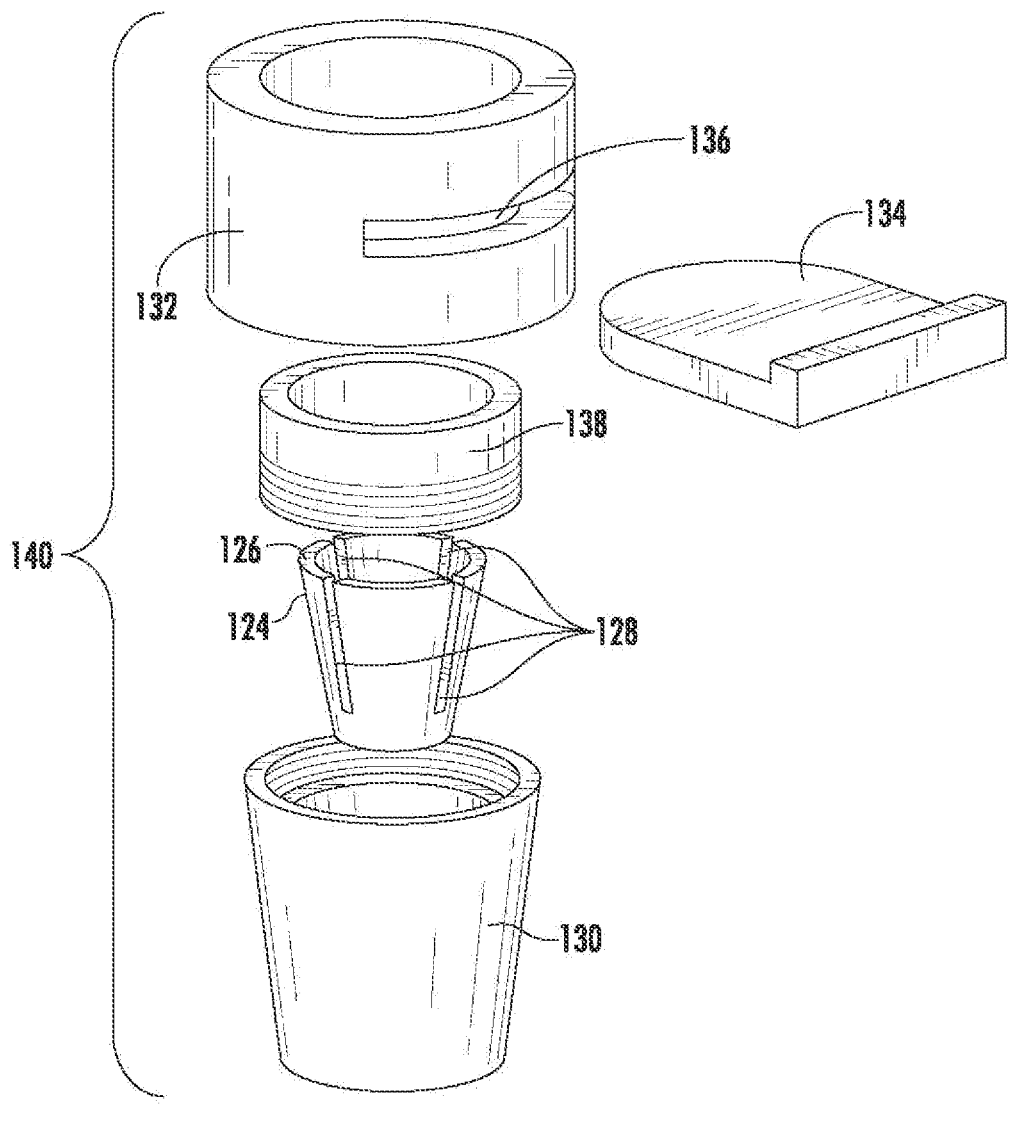
FIG. 3 is an exploded view of the filter assembly shown in FIG. 2.
Figure 4:
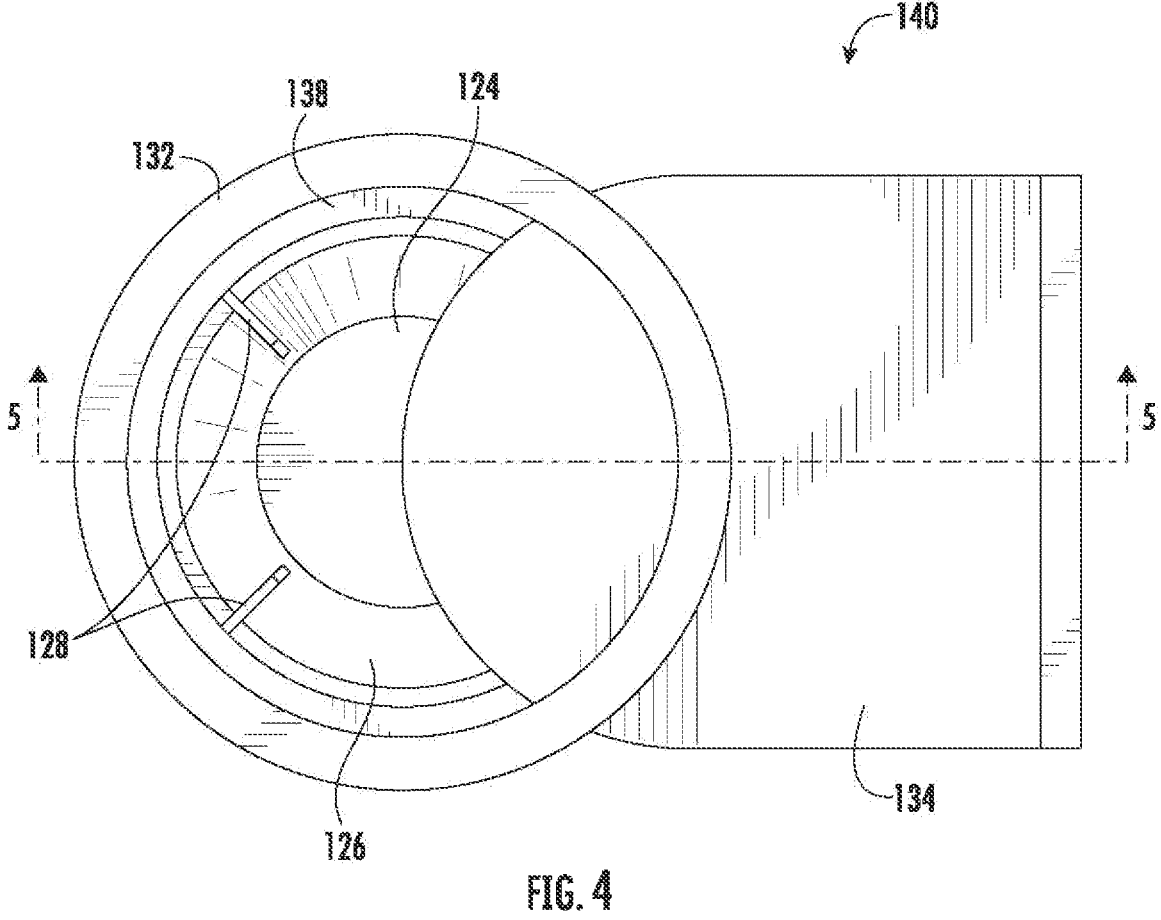
FIG. 4 is a top view of the filter assembly shown in FIG. 2 with the flow valve in the open configuration.
Figure 5:
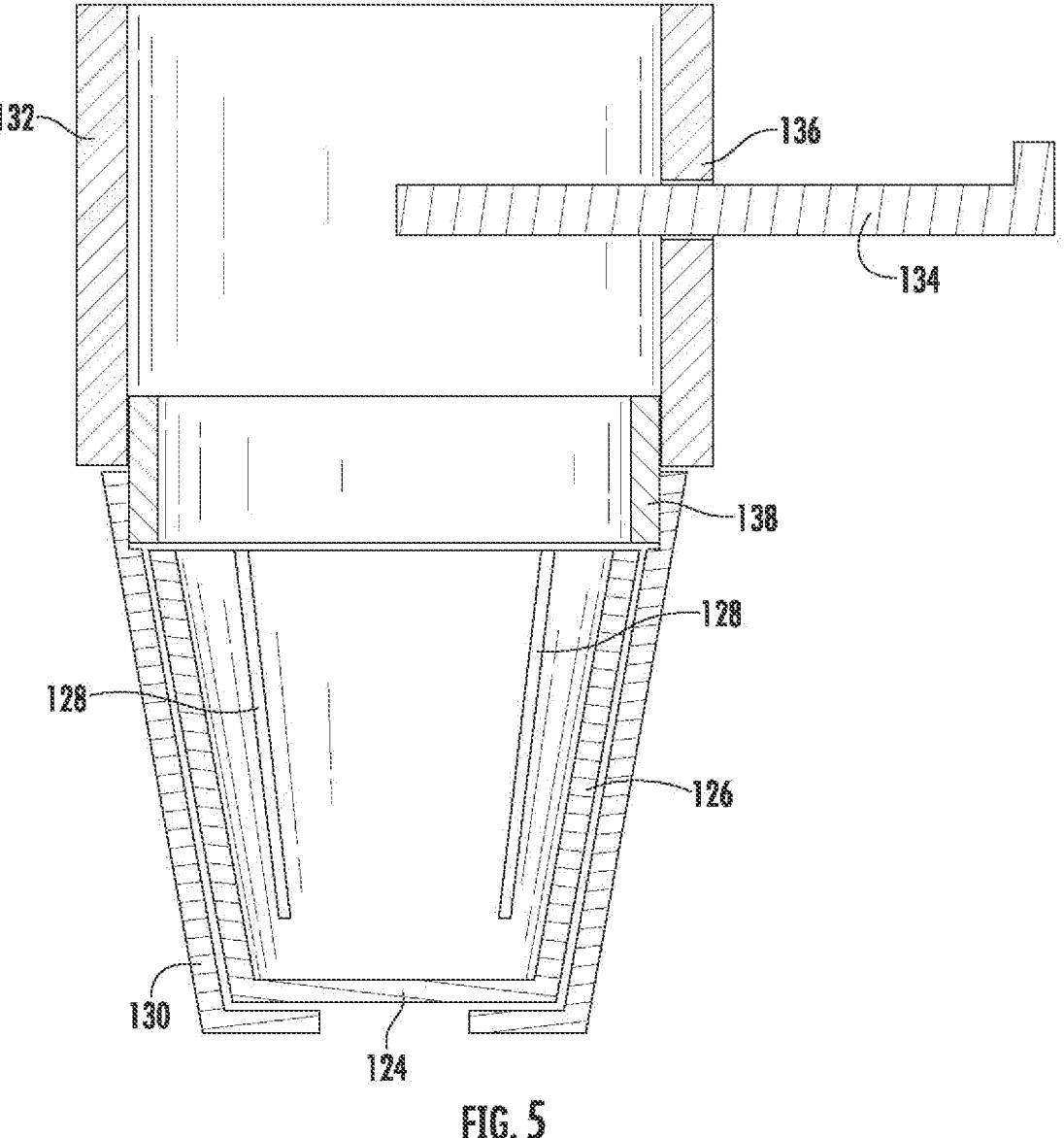
FIG. 5 is a cross section view of the filter assembly shown in FIG. 4, taken along line 5-5.
Figure 6:
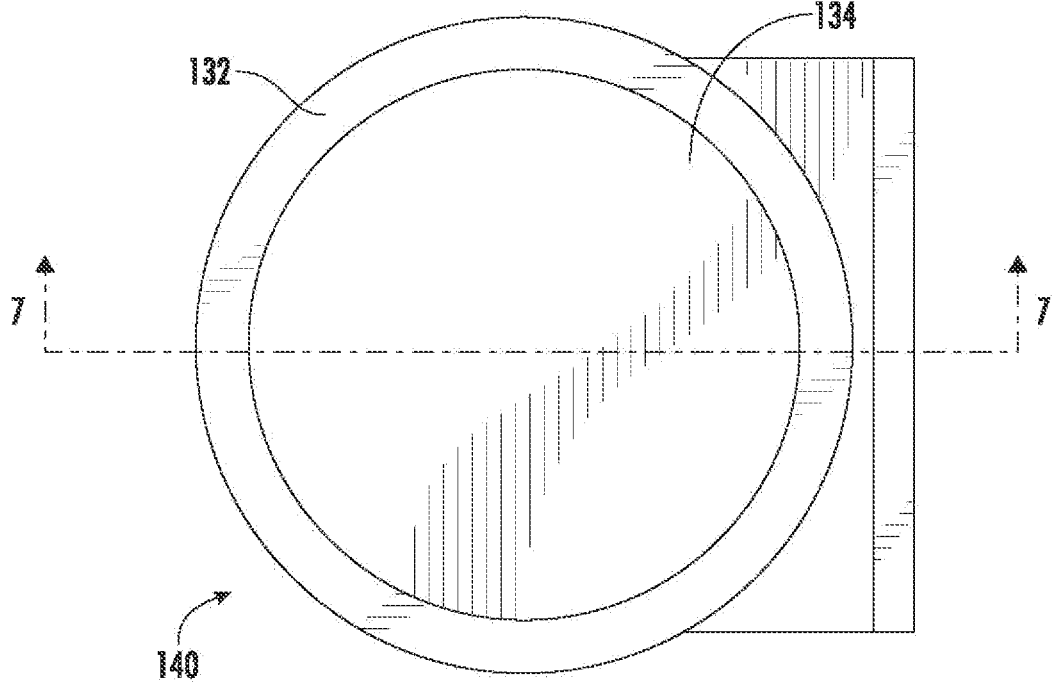
FIG. 6 is a top view of the filter assembly shown in FIG. 2 with the flow valve in the closed configuration.
Figure 7:
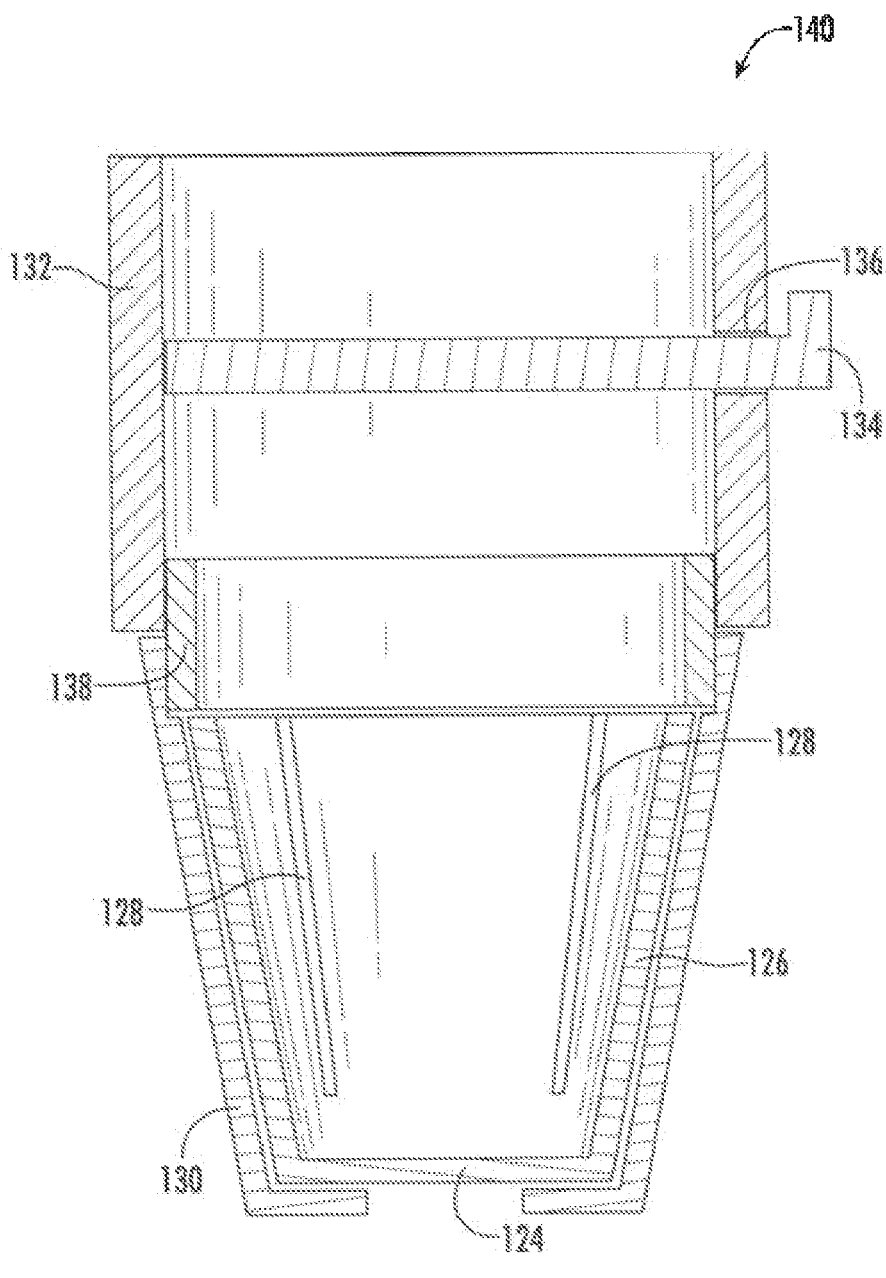
FIG. 7 is a cross section view of the filter assembly shown in FIG. 6, taken along line 7-7.

As shown in FIGS. 2-3, the blockage filter 104 may have a cup 124 that has a cup wall 126 and a plurality of slits 128 extending through the cup wall 126. In some embodiments, only one slit 128 may be implemented. The slits 128 may be sized to block any blockage material that is large enough to cause issues in the drainage tube 108. Thus, when urine flows through the blockage filter 104 by flowing into the cup 124 and then through the slits 128, the blockage material may flow with the urine and become entrapped in the cup 124. The slits 128 may be oriented to extend up the walls 126 of the cup 124. This allows the filter 104 to function for a greater amount of time because, as the filter 104 blocks blockage material from entering the drainage tube 108, the cup 124 begins to fill with blockage material. As the cup 124 fills, a greater portion of the slit 128 may be covered. In embodiments with slits 126 that extend up the cup wall 124, urine is still able to pass through the filter 104 until the cup 124 is completely full and the last portion of the slit 128 is blocked. At this point, the filter 104 or the cup 124 may be separately replaced to avoid the need to replace the entire urine collection bag assembly 100, as described in more detail below.

Additionally, the blockage filter 104 may have a filter housing 130. The cup 124 of the blockage filter 104 may be configured to sit inside of the filter housing 130, and in some embodiments, the filter housing 130 is fluidly coupled to the drainage tube 108, and thus urine that passes through the filter housing 130 is filtered through the cup 124 and then passes to the drainage tube 108. The filter housing 130 may have any shape.

The blockage filter 104 may be removable. For example, the blockage filter 104 may be threadedly coupled or otherwise removably coupled to the flow valve 110 and/or the bag 102. Thus, when the blockage filter 104 needs to be cleaned or replaced, the blockage filter 104 can be removed from the flow valve 110 or the bag 102 rather than requiring that the entire collection bag assembly 100 be replaced. For embodiments that include a flow valve 110, this may include first, moving the flow valve 110 to the closed configuration, as described in more detail below, so that flow to the blockage filter 104 is stopped while the blockage filter 104 is removed and cleaned or replaced.

The flow valve 110 is configured to selectively block the flow of urine from the bag 102 to the blockage filter 104. Thus, the flow valve 110 may have an open configuration and a closed configuration, as shown in FIGS. 4-7. When in the open configuration (FIGS. 4 and 5), the flow valve 110 permits the flow of urine from the bag 102 to the blockage filter 104 and when in the closed configuration (FIGS. 6 and 7), the flow valve 110 stops the flow of urine from the bag 102 to the blockage filter 104. In some embodiments, the flow valve 110 is positioned between the bag 102 and the blockage filter 104. Thus, the flow valve 110 may be fixedly attached to the bag 102 and may be removably coupled to the blockage filter 104 to allow the blockage filter 104 to be replaced as described above. The flow valve 110 may be a one-way valve. This may help to hinder bacteria from traveling from the patient's surroundings, through the flow valve 110, and up through the collection bag assembly 100 and into the patient, causing UTIs and other infections.

The flow valve 110 may have a body 132 and at least one valve arm 134. Each of the at least one valve arm 134 may be slidably coupled with a corresponding opening 136 in the body 132. When the flow valve 110 is moved from the open configuration to the closed configuration, the valve arm 134 may be moved further into the corresponding opening 136. Thus, to move the flow valve 110 into the open configuration from the closed configuration, the valve arm 134 must be pushed further into the corresponding opening 136 while, to move the flow valve 110 into the closed configuration, the valve arm 134 must be pulled further out of the corresponding opening 136. Each of the valve arms 134 may be locked into its corresponding opening 136 such that the valve arm 134 is restricted from completely exiting the opening 136. In some embodiments, a larger flow valve 110 may be implemented to maintain any contaminated surfaces within the flow valve 110. In addition, sealing materials and coatings are contemplated to decrease the likelihood of urine or contaminants escaping the flow valve 110.

In embodiments where the flow valve 110 is positioned at the bottom of the bag 102, blockage material that settles out of the urine within the bag 102 may tend to collect on the surfaces of the flow valve 110. In particular, if the flow valve 110 is left in the closed configuration, blockage material may build up on the valve arm 134 because the valve arm 134 is directly in the path of flow. This is not a problem unless the buildup inhibits the valve arm 134 from moving from the closed configuration to the open configuration. Thus, in some embodiments, when the flow valve 110 is moved from the closed configuration to the open configuration, the corresponding opening 136 may be configured to remove buildup from the valve arm 134. Because this motion opens up the flow valve 110 and allows urine to flow through the blockage filter 104, the blockage filter 104 catches any buildup removed from the valve arm 134 and filters it out of the urine so that the drainage tube 108 removes free of any blockage.

Figure 8:
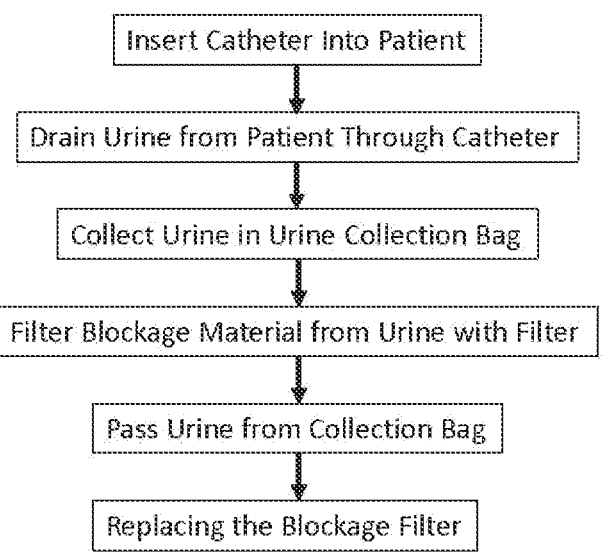
FIG. 8 is a process diagram illustrating a method of draining urine from a patient.

As illustrated in FIG. 8, a method of draining urine from a patient may comprise inserting a catheter into the patient, draining urine from the patient through the catheter, collecting the urine in a urine collection bag 102, filtering blockage material out of the urine with a blockage filter 104, and passing the urine out of the collection bag 102. As mentioned above, the blockage filter 104 may be positioned between the collection bag 102 and the drainage tube 108.

The method may also comprise replacing the blockage filter 104 with a replacement blockage filter 104. Typically, to replace the blockage filter 104, the bag 102 must be fluidly decoupled from the blockage filter 104 so that the filter 104 can be replaced without leaking urine out of the bag 102. This is the purpose of the flow valve 110, which blocks flow of urine from the bag 102 to the blockage filter 104. Once the flow valve 110 is in the closed configuration, the filter 104 can be removed and cleaned or removed and replaced by another blockage filter 104. This avoids the need to replace the entire collection bag assembly 100 and helps to maintain a barrier between the patient's environment and the urinary tract. Additionally, this removes the need for a medical professional to spend much more than a couple of second performing the change, and thus saves the patient money. Thus, the method may additionally comprise moving the flow valve 110 to a closed configuration to stop flow of urine through the blockage filter 104, replacing the blockage filter 104 with a replacement blockage filter 104 after moving the valve 110 to the closed configuration, and moving the valve 110 to an open configuration to allow flow of urine through the replacement blockage filter 104 after replacing the blockage filter 104 with the replacement blockage filter 104.

Embodiments of the present disclosure provide three primary advantages: cost-efficiency, low maintenance demands, and simplicity. The cost of replacing a urinary collection bag for a patient while in-care can vary depending on the patient, but in any case costs over a hundred to hundreds of dollars to replace when taking into account healthcare professional time and equipment. When the increased risk of infection and the cost of treating UTI infections and risk to the hospital for lawsuits and patient dissatisfaction is taken into account, the cost of the problem is ridiculously high. The solution embodied in this disclosure that enables healthcare professionals to remove blood clots in a urinary catheter collection bag drain line without replacing the entire catheter, and without additional risk of contamination or infection enables the patient and the hospital to save money, time and resources in addition to the significantly reduced risk of UTIs and the risks associated with them.

Secondly, after initial placement of the urinary catheter, maintenance of the urinary catheter collection bag for healthcare professionals is minimal. The collection bag, and associated urinary catheter, does not require replacement due to a blood clot because the simple switching of a filter immediately restores flow.

Finally, a clogged filter is easily interchangeable with a new sterile filter because of the simplistic and modular design. A healthcare professional can easily remove and replace a filter while maintaining a clean environment for themselves and their patient. The simple device minimizes patient discomfort and risk.

In hospitals and surgery centers, time and financial strains are placed on both the facility and the patients if a urinary tract infection (UTI) occurs, following the placement of a urinary catheter system. This can extend patient stays and requires more time from the provider and nurses for removing and replacing the product. Hospitals and surgery centers are likely to have less frequent occurrences of infections if they are using the urine collection bag assembly 100 with a replaceable blockage filter 104 according to this disclosure. The urine collection bag assembly 100 also has the benefit of providing a more affordable and user-friendly option for urinary catheters. The urine collection bag assembly 100 allows a patient to even empty their own bag 102 or replace their own filter 104 because it is done remote from the patient's body and does not involve re-setting the catheter into the patient's body. Additionally, the urine collection bag assembly 100 reduces common frustrations experienced by health care professionals due to blocked drains.

Manufacture of the urine collection bag assembly 100 may be accomplished using known molding techniques by those of ordinary skill in the relevant art. Because the device is used in the medical industry, medical grade materials, such as medical grade plastic, hard plastics, and plastics resistant to contaminants and infection, may be used. Bio-material filters may also be employed to further resist the spread of contamination. The blockage filter 104 and flow valve 110 may be manufactured integral with a urinary catheter and collection bag or manufactured separately and adapted for easy attachment to the collection bag as needed for particular implementations.

In some embodiments, the blockage filter 104 and the flow valve 110 may be manufactured as a replaceable filter system 140 that comprises the filter housing 130, the blockage filter 104, the flow valve 110 with a valve arm 134, and a coupler 138 for joining the blockage filter 104 to the flow valve 110. Such a system is illustrated in FIGS. 2 and 3. As discussed above, the flow valve 110 may be coupled to a lower end 114 of the urine collection bag 102 so that gravity draws the urine through the flow valve 110 and out the drainage tube 108 in fluid communication with the blockage filter 104. The various components may be coupled together according to their various purposes as needed using any methods known in the art. In particular, adhesive, such as medical grade adhesive, heat welding, press-fit, mechanical engagement, such as through, without limitation, a quarter-turn bayonet coupling or threaded coupling, are contemplated for use. Though it is not required, the coupler 138 may be permanently coupled to the flow valve 110 and removably coupled to the filter housing 130, such as through threading, with the filter 104 positioned within the combination of the coupler 138 and the filter housing 130 so that fluid flowing through the flow valve 110 passes the valve arm 134, continues through the coupler 138 and the filter 104 to then exit the system through the filter housing 130 into the associated drainage tube 108. This particular design, or another if used, may also be configured as a one-way flow valve to further resist the chances of infection or contaminants passing back up into the collection bag 102. In the medical industry, it is conventional to use tubes as drains for urinary catheter collection bags, and so it is anticipated that an appropriate tube similar to that presently used with urinary catheter collection bags will be used, but other structures may also be suitable and are contemplated in place of the drainage tube 108.

It will be understood that implementations of a urine collection bag assembly are not limited to the specific assemblies, devices and components disclosed in this document, as virtually any assemblies, devices and components consistent with the intended operation of a urine collection bag assembly may be used. Accordingly, for example, although particular urine collection bag assemblies, and other assemblies, devices and components are disclosed, such may include any shape, size, style, type, model, version, class, measurement, concentration, material, weight, quantity, and/or the like consistent with the intended operation of urine collection bag assemblies. Implementations are not limited to uses of any specific assemblies, devices and components; provided that the assemblies, devices and components selected are consistent with the intended operation of a urine collection bag assembly.

Accordingly, the components defining any urine collection bag assembly may be formed of any of many different types of materials or combinations thereof that can readily be formed into shaped objects provided that the materials selected are consistent with the intended operation of a urine collection bag assembly. For example, the components may be formed of: polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; glasses (such as quartz glass), carbon-fiber, aramid-fiber, any combination thereof, and/or other like materials; composites and/or other like materials; metals, such as zinc, magnesium, titanium, copper, lead, iron, steel, carbon steel, alloy steel, tool steel, stainless steel, brass, nickel, tin, antimony, pure aluminum, 1100 aluminum, aluminum alloy, any combination thereof, and/or other like materials; alloys, such as aluminum alloy, titanium alloy, magnesium alloy, copper alloy, any combination thereof, and/or other like materials; any other suitable material; and/or any combination of the foregoing thereof. In instances where a part, component, feature, or element is governed by a standard, rule, code, or other requirement, the part may be made in accordance with, and to comply under such standard, rule, code, or other requirement.

Various urine collection bag assemblies may be manufactured using conventional procedures as added to and improved upon through the procedures described here. Some components defining a urine collection bag assembly may be manufactured simultaneously and integrally joined with one another, while other components may be purchased pre-manufactured or manufactured separately and then assembled with the integral components. Various implementations may be manufactured using conventional procedures as added to and improved upon through the procedures described here.

Accordingly, manufacture of these components separately or simultaneously may involve extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled with one another in any manner, such as with adhesive, a weld, a fastener (e.g. a bolt, a nut, a screw, a nail, a rivet, a pin, and/or the like), wiring, any combination thereof, and/or the like for example, depending on, among other considerations, the particular material forming the components.

It will be understood that methods for manufacturing or assembling urine collection bag assemblies are not limited to the specific order of steps as disclosed in this document. Any steps or sequence of steps of the assembly of a urine collection bag assembly indicated herein are given as examples of possible steps or sequence of steps and not as limitations, since various assembly processes and sequences of steps may be used to assemble urine collection bag assemblies.

The implementations of a urine collection bag assembly described are by way of example or explanation and not by way of limitation. Rather, any description relating to the foregoing is for the exemplary purposes of this disclosure, and implementations may also be used with similar results for a variety of other applications employing a urine collection bag assembly.

What is claimed is:

1. A urinary catheter urine collection bag assembly, comprising:
   a bag having an upper end with an inlet and a lower end opposite the upper end with an outlet;
   a urinary catheter fluidly coupled to the inlet and configured to pass urine from a patient to the bag;
   a drainage tube fluidly coupled to the outlet and configured to pass urine out of the bag;
   a removable blockage filter positioned between the bag and the drainage tube and configured to filter the urine before the urine passes through the drainage tube, the blockage filter having a cup with a cup wall and a plurality of slits extending through the cup wall; and
   a flow valve positioned between the bag and the blockage filter and removably coupled to the blockage filter, wherein the flow valve is configured to selectively block the flow of urine from the bag to the blockage filter, the flow valve having an open configuration in which the flow of urine through the flow valve is permitted and a closed configuration in which the flow of urine through the flow valve is stopped.

2. The urine collection bag assembly of claim 1, wherein the flow valve is a one-way valve.

3. The urine collection bag assembly of claim 1, the blockage filter further having a filter housing fluidly coupled to the drainage tube, wherein the cup is configured to sit inside of the filter housing.

4. The urine collection bag assembly of claim 1, the flow valve having a body and at least one valve arm slidably coupled with a corresponding opening in the body, wherein when the flow valve is moved from the open configuration to the closed configuration, the at least one valve arm is moved further into the corresponding opening.

5. The urine collection bag assembly of claim 4, wherein when the flow valve is moved from the closed configuration to the open configuration, the corresponding opening is configured to remove buildup on the at least one valve arm from the at least one valve arm.

6. A urinary catheter urine collection bag assembly, comprising:

a bag having a lower end with an outlet;

a urinary catheter fluidly coupled to the bag and configured to pass urine from a patient to the bag;

a drainage tube fluidly coupled to the outlet and configured to pass urine out of the bag; and a blockage filter positioned between the bag and the drainage tube and configured to filter the urine before the urine passes through the drainage tube.

7. The urine collection bag assembly of claim 6, wherein the blockage filter is removable.

8. The urine collection bag assembly of claim 6, the blockage filter having a cup with a cup wall and a plurality of slits extending through the cup wall.

9. The urine collection bag assembly of claim 8, the blockage filter further having a filter housing fluidly coupled to the drainage tube, wherein the cup is configured to sit inside of the filter housing.

10. The urine collection bag assembly of claim 6, further comprising a flow valve positioned between the bag and the blockage filter and removably coupled to the blockage filter, wherein the flow valve is configured to selectively block the flow of urine from the bag to the blockage filter.

11. The urine collection bag assembly of claim 10, the flow valve having an open configuration in which the flow of urine through the flow valve is permitted and a closed configuration in which the flow of urine through the flow valve is stopped.

12. The urine collection bag assembly of claim 11, the flow valve having a body and at least one valve arm slidably coupled with a corresponding opening in the body, wherein when the flow valve is moved from the open configuration to the closed configuration, the at least one valve arm is moved further into the corresponding opening.

13. The urine collection bag assembly of claim 12, wherein when the flow valve is moved from the closed configuration to the open configuration, the corresponding opening is configured to remove buildup on the at least one valve arm from the at least one valve arm.

14. The urine collection bag assembly of claim 10, wherein the flow valve is a one-way valve.

15. A method of draining urine from a patient, comprising:

inserting a catheter into the patient;

draining urine from the patient through the catheter;

collecting the urine in a urine collection bag;

filtering blockage material out of the urine with a blockage filter after collecting the urine in the urine collection bag; and passing the urine out of the collection bag.

16. The method of claim 15, further comprising replacing the blockage filter with a replacement blockage filter.

17. The method of claim 15, wherein the blockage filter is positioned between the collection bag and a drainage tube.

18. The method of claim 15, further comprising moving a valve to a closed configuration to stop flow of urine through the blockage filter.

19. The method of claim 18, further comprising replacing the blockage filter with a replacement blockage filter after moving the valve to the closed configuration.

20. The method of claim 19, further comprising moving the valve to an open configuration to allow flow of urine through the replacement blockage filter after replacing the blockage filter with the replacement blockage filter.

* * * * *